US009220271B2

(12) United States Patent
Shroff et al.

(10) Patent No.: US 9,220,271 B2
(45) Date of Patent: Dec. 29, 2015

(54) NON-DUSTY, FREE FLOWING, STORAGE STABLE SOLID COMPOSITION AND A PROCESS FOR ITS PREPARATION

(75) Inventors: Jaidev Rajnikant Shroff, Mumbai (IN); Vikram Rajnikant Shroff, Mumai (IN); Prakash Mahadev Jadhav, Mumbai (IN); Sujata Dhondiram Desai, Dist. Satara (IN)

(73) Assignee: UPL Limited, Mumbai (IN)

( * ) Notice: Subject to any disclaimer, the term of this patent is extended or adjusted under 35 U.S.C. 154(b) by 1833 days.

(21) Appl. No.: 12/155,985

(22) Filed: Jun. 12, 2008

(65) Prior Publication Data

US 2008/0312320 A1     Dec. 18, 2008

Related U.S. Application Data

(60) Provisional application No. 60/944,147, filed on Jun. 15, 2007.

(51) Int. Cl.
*A01N 53/00* (2006.01)
*A01N 25/08* (2006.01)
*A01N 25/14* (2006.01)
*A01N 25/30* (2006.01)

(52) U.S. Cl.
CPC ..................... *A01N 53/00* (2013.01)

(58) Field of Classification Search
CPC ....... A01N 53/00; A01N 25/08; A01N 25/14; A01N 25/30
See application file for complete search history.

(56) References Cited

U.S. PATENT DOCUMENTS

| 5,326,573 | A | * | 7/1994 | Antfang et al. ............. 424/490 |
| 5,550,179 | A | * | 8/1996 | Srourian ..................... 524/210 |
| 5,705,193 | A |   | 1/1998 | Bourgogne |
| 2003/0130233 | A1 | * | 7/2003 | Hill ............................. 514/67 |

FOREIGN PATENT DOCUMENTS

| EP | 0127773 | 12/1984 |
| JP | 2003-95810 | 4/2003 |
| WO | 89/00079 | 1/1989 |
| WO | 90/07275 | 7/1990 |
| WO | 96/36226 | 11/1996 |
| WO | 2005/039288 | 5/2005 |

OTHER PUBLICATIONS

Permethrin MSDS accessed Nov. 16, 2011 from http://msds.chem.ox.ac.uk/PE/permethrin.html, updated Sep. 5, 2003, p. 1-3.*
Cyfluthrin MSDS accessed Nov. 16, 2011 from http://pmep.cce.cornell.edu/profiles/extoxnet/carbaryl-dicrotophos/cyfluthrin-ext.html, updated Oct. 1995, p. 1-6.*
Tau-fluvalinate Crop Protection Dictionary, http://sitem.herts.ac.uk/aeru/iupac/Reports/617.htm accessed Nov. 16, 2011, © 2011, p. 1.*
Tefluthrin data sheet PPDB, http://sitem.herts.ac.uk/aeru/iupac/Reports/617.htm accessed Nov. 16, 2011, updated Sep. 1, 2011, p. 1-7.*
Tralomethrin, Crop Protection Dictionary, © 2011, http://www.farmchemicalsinternational.com/cropprotection/cpd/?op=cpdproductdetail&pid=400200 accessed Nov. 16, 2011, p. 1-2.*
Fluvalinate MSDS, http://pmep.cce.cornell.edu/profiles/extoxnet/dienochlor-glyphosate/flucythrinate-ext.html accessed Nov. 16, 2011, published Sep. 1993, p. 1-5.*
Fenvalerate research document accessed via http://pmep.cce.cornell.edu/profiles/insect-mite/fenitrothion-methylpara/fenvalerate/insect-extox-fenvalerate.html accessed Nov. 16, 2011, p. 1-5.*
Esfenvalerate MSDS, published May 1994, accessed via http://pmep.cce.cornell.edu/profiles/extoxnet/dienochlor-glyphosate/esfenvalerate-ext.html accessed Nov. 16, 2011, p. 1-6.*
Flucythrinate MSDS, published Sep. 1993, accessed via http://pmep.cce.cornell.edu/profiles/extoxnet/dienochlor-glyphosate/flucythrinate-ext.html accessed Nov. 16, 2011, p. 1-6.*
Lambda-Cyhalothrin MSDS, revised 1996, accessed via http://extoxnet.orst.edu/pips/lambdacy.htm accessed Nov. 16, 2011, p. 1-5.*

* cited by examiner

*Primary Examiner* — Bethany Barham
*Assistant Examiner* — Barbara Frazier
(74) *Attorney, Agent, or Firm* — Yancy IP Law, PLLC

(57) ABSTRACT

A solid water dispersible granular composition of pesticide comprising up to 50% of at least one pesticide from pyrethroid class, more particularly a highly viscous liquid pyrethroid insecticide, permethrin, having the properties of excellent dispersibility and suspensibility, as well as the process of preparation of the composition are disclosed. Also the improved storage stability, dispersibility and suspensibility properties are discussed for this granular composition.

7 Claims, No Drawings

NON-DUSTY, FREE FLOWING, STORAGE STABLE SOLID COMPOSITION AND A PROCESS FOR ITS PREPARATION

CROSS-REFERENCE TO RELATED APPLICATIONS

This application claims the benefit, under 35 U.S.C. 119 (e), of U.S. Provisional Application No. 60/944,147, the contents of which are incorporated herein by reference.

BACKGROUND OF THE INVENTION

1. Field of Invention

The proposed invention relates to a non dusty, free flowing, storage stable solid composition. This invention particularly relates to a non dusty, free flowing, storage stable solid composition comprising of at least one pesticide from pyrethroid class like cypermethrin, fenvalerate, permethrin, alphacypermethrin, betacypermethrin, zetacypermethrin, deltamethrin, cyfluthrin, low melting solid pyrethroids like bifenthrin, lambda cyhalothrin, and/or bioresmethrin, more particularly a high viscous liquid insecticide like permethrin. More particularly, this invention relates to a stable composition with improved properties of dispersibility and suspensibility brought about by a combination of inert ingredients silica and kaolin along with block copolymer of ethylene oxide and propylene oxide in specific proportions. The present invention also relates to a process of preparing the said composition.

2. Description of Related Art

Solid compositions like granules are mainly produced by methods such as kneading, extrusion granulation, impregnation, coating etc. Granules are more frequently applied to water surface or soil than directly applied to target crops. After application to water surface or soil, the active ingredient of granules dissolves/disperses in water or vaporizes to reach its action sites and displays the effect. It is therefore required that the same water dispersibility and suspensibility as those at the time of formulation are maintained even after long term storage.

Dry powdery (like wettable powder WP and others) composition has disadvantages like presence of sediment at the bottom of dilution tank, choking of nozzle while spraying, lumping during storage and drift problem at the time of production, packing, transportation, storage, handling, dilution and use.

Generally in liquid formulations like emulsifiable concentrates (EC), soluble liquid (SL), Microemulsions (ME), and capsule suspensions (CS) etc., the composition involves the use of organic solvents like petroleum ether, hydrocarbon solvents, xylene, isopropyl alcohol etc., which may cause further problems like toxicity, irritation to human body and/or other associated problems due to their physico-chemical properties like flash point, solvency with other materials, flammable and reactive nature.

All liquid compositions (like emulsifiable concentrates EC and others) which have been used in agriculture or veterinary applications comprising liquid pyrethroids of concentrations more than 20% suffer with high volatility due to volatile contents and comprise flammable solvents. Organic solvents are most commonly used as inert solvents. Suitable as liquid solvents, are aromatic hydrocarbons, such as xylene, toluene or alkyl naphthalenes; chlorinated aromatic hydrocarbons and chlorinated aliphatic hydrocarbons, such as chlorobenzenes, methylene chloride; aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone; strongly polar solvents, such as dimethylformamide and dimethylsulphoxide. Some of these solvents are agriculturally unacceptable, and need to be used in low or high concentrations to produce formulations of desired strength, which can be diluted and applied to the target areas to control pest effect. Selection and use of the solvent is based on the solubility criteria for active ingredients which sometimes require a single solvent or a combination of solvents as per the type and strength of the formulation product.

WO 9007275, discloses a dry herbicidal composition comprising a water soluble salt of N-phosphonomethylglycine as a water dispersible granule, water soluble granule, water dispersible powder or water soluble powder. The composition comprises a water soluble salt of N-phosphonomethylglycine and additionally one or more liquid surfactants. This invention requires a preparation of herbicidal water soluble salt during the process from its acid derivative (which is solid in physical form) or a water soluble salt (in solid physical form) as one of the main ingredients.

Prior art, Japanese patent 2003095810, discloses the wettable granules comprising liquid pesticidal active ingredient, solvent, emulsifier, dispersion agent and surfactant. This invention requires the use of solvent so that the active ingredient gets uniformly distributed over the inert ingredients.

Also, prior art EP127773, discloses tablet preparation of a pesticidal composition comprising a pesticide, an emulsifier or dispersing agent for the pesticide and a self disintegrating agent capable of effervescing or swelling on being contacted with water. The pesticide disclosed is a synthetic pyrethroid from 1-20% by weight. This invention requires a self disintegrating agent which is capable of effervescing or swelling on being contacted with water. Methylene dichloride is used as a solvent for the active ingredient and the simple mixing process is done to mix a solution of above active ingredient and other ingredients comprising emulsifier or dispersing agent, lubricants, surfactants and antifoaming agents. Then the granule formation is done followed by tablet formation.

The preparation of granules via an extrusion process is well known. Most of the known processes extrude a premix of active material and other ingredients under relatively high pressure, (and generally in excess of 100 psi) and cut the spaghetti like extrudate into short lengths. These may be subsequently dried. An alternative process is disclosed in copending application PCT AU 88/00201 which uses low pressure extrudation (<30 ps of a wet mix having relatively high levels of water. This leads to an extrudate of low compactness which readily breaks into small segments by gentle rolling or tumbling action which also tends to round the ends of the granules. Again these granules may be subsequently dried.

Granules may also be prepared by coating a core granule with an absorbent coating of filler particles. A liquid active material may then be loaded onto the surface layer of the granules. Such a process is disclosed in NZ Patent 154,193 where the objective was to produce granules with reduced absorptive properties compared to granules prepared from minerals such as attapulgite. However these granules are designed for direct application to soil, pastures or other locus and as they have cores of particle size approximately 250 μm they would not be suitable for use as WG as the granule would not pass through the spray nozzle.

Also the basic method of preparing granules involves a preliminary step of forming a wettable powder by blending the ingredients and milling them to provide the desired particle size. The wettable powder is then subsequently formed into granules by a range of techniques including agglomeration, spray drying, or other means such as pan granulation.

It is not always possible to achieve good dispersibility and shelf life with all formulations especially with compositions where the biologically active agent is in a liquid state and relatively high levels of active agent are included in the granule. There is thus a need for alternative granulation methods in order to enable a wider spectrum of liquid pesticides to be formulated in an effective and economical manner. Also there is a need for a non dusty, free flowing, storage stable solid compositions comprising pyrethroid type insecticides, more particularly semi viscous liquid pyrethroid which results in a stable dispersion in presence of water. It is well-known that the preparation of a DF formulation with liquid active using the standard inert excipients is quite difficult for over 10% active. The prior art teaches maximum of 25 EC and 25 WP for actives like Permethrin but no DF formulations exist in the market. The present invention takes care of all these problems of dry WP, solid/granular, tablet/pellets formulations given in prior art and provides for higher concentrations of liquid actives for DF formulations.

BRIEF SUMMARY OF THE INVENTION

Silica and kaolin are traditionally known as inert fillers while the block copolymer of ethylene oxide and propylene oxide is traditionally known for its use as a surfactant. Surprisingly it was found that when these were used in a definite ratio they imparted properties of good suspensibility and dispersibility to the formulation and also enabled in formulating high concentrations of the liquid active ingredient into free-flowing granular form. The solid compositions of the proposed invention have excellent storage stability, dispersibility and suspensibility even after comprising high concentrations of pesticides from pyrethroid class.

In the present invention no solvent is used during granule formulation so there is no risk of flammability and irritation to the body. Generally, during formulation, organic solvents like petroleum ether, isopropyl alcohol etc. are used which may cause irritation to human body. Problems due to their flammable nature are avoided in present invention by avoiding the use of organic solvents. The inventors have discovered that the liquid active ingredient when dissolved in the surfactant allows the adsorbed active ingredient to disperse well at the time of dilution with water. The inventors of the present invention have additionally discovered the surprising effect of the synergistic action of the combined use of inert ingredients silica and kaolin which normally function only as fillers along with block copolymer of ethylene oxide and propylene oxide which normally functions only as a surfactant. When used together in a definite ratio, they imparted properties of good suspensibility and dispersibility to the formulation and also enabled in formulating high concentrations of the liquid active ingredient into free-flowing granular form. In addition, the present invention avoids excessive dust formation during operation by skipping the grinding process.

The main objective of the proposed invention is to provide a non dusty, free flowing, storage stable solid composition devoid of the draw backs of the hitherto known composition.

Another objective of the proposed invention is to provide non dusty, free flowing, storage stable solid composition having the properties of storage stability, excellent dispersibility and suspensibility.

Yet another objective of the proposed invention is to provide a non dusty, free flowing, storage stable solid composition comprising at least one pesticide from pyrethroid class like cypermethrin, fenvalerate, permethrin, alphacypermethrin, betacypermethrin, zetacypermethrin, deltamethrin, cyfluthrin, bifenthrin, lambda-cyhalothrin, and/or bioresmethrin.

Yet another objective of the proposed invention is to provide non dusty, free flowing, storage stable solid composition having the properties of excellent dispersibility and suspensibility using at least a liquid surfactant selected from polyoxyethlene alkyl ether group.

Another objective of the proposed invention is to provide non dusty, free flowing, storage stable solid composition having the properties of excellent dispersibility and suspensibility in solid form preferably in water dispersible granular form.

Yet another objective of the proposed invention is to provide a process for the preparation of non dusty, free flowing, storage stable solid composition which is a relatively inexpensive and environmentally safe.

Yet another objective of the proposed invention is to provide a process for the preparation of non dusty, free flowing, storage stable solid composition in water dispersible granular form which are not prone to dust generation while filling in bags and transportation, thereby avoiding polluting the environment.

Another objective of the proposed invention is to provide a process for the preparation of non dusty, free flowing, storage stable solid composition in water dispersible granular form by using the liquid pesticide.

Yet another objective of the proposed invention is to provide a process for the preparation of non dusty, free flowing, storage stable solid composition in water dispersible granular form by using at least a liquid pesticide and at least one liquid surfactant.

Yet another objective of the proposed invention is to provide a process for the preparation of non dusty, free flowing, storage stable solid composition without using any solvents.

The above mentioned objectives of the proposed invention have been achieved by our sustained R & D due to our finding that in solid composition comprising pyrethroids, the use of liquid surfactants selected from polyoxyethlene alkyl ether group and when this composition is coated on a mixture of Kaolin and precipitated silica as an inert filler in selected ratio provides good dispersibility and suspensibility to the resulting solid composition. Also kaolin, which normally acts as inert filler, acts as a carrier in the composition of the present invention due to adsorption process. In addition to this, silica, which is normally used as an adsorbent, functions as an anticaking agent.

Accordingly, the proposed invention provides a non dusty, free flowing, storage stable solid composition which comprises a mixture of kaolin and precipitated silica having a coating of a composition comprising at least one pesticide selected from pyrethroid class like cypermethrin, fenvalerate, permethrin, alphacypermethrin, betacypermethrin, zetacypermethrin, deltamethrin, cyfluthrin, bifenthrin, lambda-cyhalothrin, and/or bioresmethrin and at least one liquid surfactant selected from polyoxyethlene alkyl ether group.

According to another aspect of the proposed invention, there is provided a process for the preparation of a non dusty, free flowing, storage stable solid composition which comprises:

(i) mixing an active ingredient selected from at least one pesticide selected from pyrethroid class like cypermethrin, fenvalerate, permethrin, alphacypermethrin, betacypermethrin, zetacypermethrin, deltamethrin, cyfluthrin, bifenthrin, lambda-cyhalothrin, and/or bioresmethrin with at least one liquid nonionic surfactant selected from polyoxyethlene alkyl ether group and one anionic surfactant selected from salt of alkyl aryl sulphonate group (i.e. calcium salt of dodecyl benzene sulphonate) to obtained a liquid mixture;

(ii) mixing the powder of kaolin, precipitated silica, wetting agent, dispersing agent, and a binder;

(iii) adding the liquid mixture obtained in step (i) to a mixing vessel containing the powder prepared described in step (ii);

(iv) mixing thoroughly the ingredients of step (iii);

(v) granulating the resulting mixture obtained in step (iv);

(vi) sieving, if required, to obtain the desired sizes of the solid composition; and (vii) drying, if required, the resulting solid composition.

DETAILED DESCRIPTION OF THE INVENTION

The present invention is broadly related to free-flowing solid compositions of high concentrations of liquid pyrethroid pesticides with good suspensibility and dispersability properties. These properties are achieved by the combined use of inert ingredients silica and kaolin along with polyoxyethylene alkyl ether or block copolymer of ethylene oxide and propylene oxide. Silica and kaolin are traditionally known as fillers and block copolymer of ethylene oxide and propylene oxide is traditionally known for its use as a surfactant for liquid compositions. Surprisingly it was found that when the block copolymer of ethylene oxide and propylene oxide when combined with silica and kaolin in a definite ratio, imparted properties of good suspensibility and dispersibility to the formulation and also enabled in formulating high concentrations of the liquid active ingredient into free-flowing granular form.

Granules prepared by using other solid surfactants such as sodium naphthalene sulfonate, naphthalene formaldehyde condensate, castor oil ethoxylates and like which are known for their use in solid granular formulations, were not able to provide good dispersability to the final composition. Even liquid surfactants like castor oil ethoxylate and alkyl phenol ethoxylate did not impart the required dispersibility and suspensibility to the high active pesticidal compositions of the present invention.

Experiments were conducted to select and evaluate the inert fillers of at least some oil absorption value of 75 to make the dry flowable particulates of up to 50% liquid active. Inert clay kaolin and silica were evaluated individually for their effect on granule formation.

Kaolin has a liquid holding capacity (LHC) or oil absorbtion of 10-20%;

TABLE 1

Effect of various concentrations of inert clay kaolin on granulation of various concentrations of active ingredient.

| Sr No | % active | Kaolin % | Observations |
|---|---|---|---|
| 1 | 0.11 | 80.56 | (A) |
| 2 | 0.53 | 79.64 | (A) |
| 3 | 5.32 | 73.35 | (A) |
| 4 | 26.66 | 46.01 | (B) |
| 5 | 31.92 | 40.75 | (C) |
| 6 | 37.24 | 35.43 | (C) |
| 7 | 42.56 | 30.11 | (C) |
| 8 | 47.88 | 18.79 | (C) |
| 9 | 53.20 | 13.47 | (C) |

(A) Good granules with bulk density ranging from 0.650 to 0.720 g/ml and wet sieve test: 99% passing through 75μ (200 BSS).
(B) Slightly soft sticky granules with bulk density ranging from 0.543 to 0.589 g/ml and wet sieve test: 89% passing through 75μ (200 BSS).
(C) Soft and Sticky granules with bulk density ranging from 0.513 to 0.532 g/ml and wet sieve test: 78% passing through 75μ (200 BSS).

Inert filler silica with liquid holding capacity (LHC) or oil absorption of 120 to 180% was evaluated and following observations were made.

TABLE 2

Effect of various concentrations of silica on granulation of various concentrations of active ingredient.

| Sr No | % age active | Silica % | Observations | Ratio % active:% silica |
|---|---|---|---|---|
| 1 | 0.1064 | 2 | (A) | 1:18.796 |
| 2 | 1.064 | 3 | (A) | 1:2.819 |
| 3 | 5.32 | 4 | (A) | 1:0.752 |
| 4 | 10.64 | 5 | (A) | 1:0.469 |
| 5 | 15.96 | 7 | (A) | 1:0.439 |
| 6 | 26.66 | 10 | (A) | 1:0.376 |
| 7 | 37.24 | 12 | (A) | 1:0.322 |
| 8 | 42.56 | 12 | (A) | 1:0.282 |
| 9 | 47.88 | 20 | (B) | 1:0.418 |
| 10 | 53.20 | 20 | (B) | 1:0.376 |

(A) Good granules with bulk density ranging from 0.640 to 0.710 g/ml and wet sieve test: 99% passing through 75μ (200 BSS).
(B) Soft and Sticky granules with bulk density ranging from 0.510 to 0.538 g/ml and wet sieve test: 78% passing through 75μ (200 BSS).

The above table indicates that individual clay alone is not able to help in good granule formation. Also random selection of a mixture could not be used.

Individual clays/inerts were evaluated for their oil absorption or liquid holding capacity and compared with reported values.

Clay minerals of the montmorillonite group, based on a three layer structure comprising two tetragonal layers of $SiO_4$ sandwiching an octagonal layer of $AlO_6$ between them, and a plurality of such basic three-layer structures were also evaluated. Montmorillonite has a liquid holding capacity (LHC) or oil absorption of 30-70%.

TABLE 3

Effect of various concentrations of inert clay montmorillonite on granulation of various concentration of active ingredients.

| No. | Clay - Montmorillonite | % age active | Observations |
|---|---|---|---|
| 1 | 60.46 | 15.96 | A |
| 2 | 46.82 | 26.60 | B |
| 3 | 41.5 | 31.92 | B |
| 4 | 30.86 | 42.56 | B |
| 5 | 14.22 | 53.20 | B |

(A) Good granules with bulk density ranging from 0.635 to 0.715 g/ml and wet sieve test: 99% passing through 75μ (200 BSS).
(B) Soft and Sticky granules with bulk density ranging from 0.505 to 0.550 g/ml and wet sieve test: 75% passing through 75μ (200 BSS).

Bentonite is a naturally occurring, white calcium clay. Due to its thixotropic properties, bentonite functions as a thickening and/or suspension agent in water and solvent paints.

TABLE 4

Effect of various concentrations of inert clay Bentonite on granulation of various concentration of active ingredients.

| Clay - Bentonite | % age active | Observations |
|---|---|---|
| 1 | 60.46 | 15.96 | A |
| 2 | 46.82 | 26.60 | B |
| 3 | 36.18 | 37.24 | B |
| 4 | 30.86 | 42.56 | B |
| 5 | 19.54 | 47.88 | B |

(A) Good granules with bulk density ranging from 0.642 to 0.711 g/ml and wet sieve test: 99% passing through 75μ (200 BSS).
(B) Soft and Sticky granules with bulk density ranging from 0.517 to 0.548 g/ml and wet sieve test: 77% passing through 75μ (200 BSS).

It is thus seen that not any individual clay can be used. Also random selection of mixture cannot be used.

TABLE 5

Comparision of oil absorbtion or liquid holding capacity of Reported LHC cc/gram with Evaluated LHC cc/gram

|  | Reported LHC cc/gram | Evaluated LHC cc/gram |
| --- | --- | --- |
| Kaolin | 30-70 | 10-20 |
| Silica | 180-200 | 120-140 |
| Bentonite | 40-70 | 10-15 |
| Montmorillonite | 30-70 | 10-20 |

Then kaolin and silica combination was evaluated for their combined LHC and observations were tabulated.

TABLE 6

Ratio of Silica + Kaolin mixture for absorption of liquid active in higher concentrations.

| Sr No | % active | % silica:kaolin | Observations | Ratio of % Active:% silica + Kaolin |
| --- | --- | --- | --- | --- |
| 1 | 0.1 | 2 + 81.31 | (A) | 1:782.9 |
| 2 | 1.064 | 3 + 79.36 | (A) | 1:77.41 |
| 3 | 5.32 | 4 + 74.10 | (A) | 1:14.68 |
| 4 | 10.64 | 5 + 67.78 | (A) | 1:6.840 |
| 5 | 15.96 | 7 + 60.48 | (A) | 1:4.228 |
| 6 | 26.60 | 10 + 46.82 | (A) | 1:2.136 |
| 7 | 37.24 | 12 + 36.18 | (A) | 1:1.294 |
| 8 | 42.56 | 12 + 30.86 | (A) | 1:1.007 |
| 9 | 47.88 | 20 + 19.54 | (B) | 1:0.826 |
| 10 | 53.20 | 20 + 14.22 | (B) | 1:0.643 |

(A) Good granules with bulk density ranging from 0.649 to 0.719 g/ml and wet sieve test: 99% passing through 75μ (200 BSS).
(B) Soft and Sticky granules with bulk density ranging from 0.520 to 0.545 g/ml and wet sieve test: 78% passing through 75μ (200 BSS).
Best ratio(s) of silica:kaolin are placed in between 1:1 to 1:40 for formation of good granules.

The above chosen combination of inerts was used to adsorb the liquid active but it was found that the limitation of the DF formulation was its non-dispersibility and non-suspensibility.

Traditionally known surfactants were tried out to improve the non-dispersibility.

TABLE 7

Composition using traditional Solid surfactants

| Sr. No. | Ingredients | A | B | C |
| --- | --- | --- | --- | --- |
| 1 | Permethrin Technical | 26.60 | 26.60 | 26.60 |
| 2. | Sodium naphthalene formaldehyde condensate | 0.00 | 8.00 | 0.00 |
| 3 | Dioctyl sulfosuccinate | 0.00 | 0.00 | 8.00 |
| 4 | Styrene acrylic copolymer | 8.00 | 0.00 | 0.00 |
| 5 | Kaolin | 46.05 | 45.65 | 46.65 |
| 6 | Sodium Naphtalene sulphonate | 5.00 | 5.00 | 5.00 |
| 7 | Dimethyl poly siloxane 30% emulsion | 0.50 | 0.50 | 0.50 |
| 8 | Poly vinyl pyrrolidone | 0.25 | 0.25 | 0.25 |
|  | Comments: | Suspensibility & Dispersibility of granules are very low. | Suspensibility & Dispersibility of granules are very low. | Suspensibility & Dispersibility of granules are very low. |

All the above solid surfactants when used individually failed to impart the requisite dispersibility. In fact none of the solid surfactants worked alone or in mixtures.

Even the traditional liquid surfactants were unable to give the required dispersibility and suspensibility.

TABLE 8

Effect of traditional liquid surfactants on dispersibility and suspensibility of the DF composition.

| Sr. No. | Ingredients | A | B | C |
| --- | --- | --- | --- | --- |
| 1 | Permethrin Technical | 26.60 | 26.60 | 26.60 |
| 2. | Ethoxylated caster oil 40 moles | 2.75 | 0.00 | 0.00 |
| 3 | Calcium dodecyl benzene sulphonate | 0.85 | 1.00 | 0.75 |
| 4 | Precipitated silica | 10.00 | 10.00 | 10.00 |
| 5 | Kaolin | 46.05 | 45.65 | 46.65 |
| 6 | Sodium Naphtalene sulphonate | 5.00 | 5.00 | 5.00 |

TABLE 8-continued

Effect of traditional liquid surfactants on dispersibility and suspensibility of the DF composition.

| Sr. No. | Ingredients | A | B | C |
|---|---|---|---|---|
| 7 | Styrene acrylic copolymer | 8.00 | 8.00 | 8.00 |
| 8 | Dimethyl poly siloxane 30% emulsion | 0.50 | 0.50 | 0.50 |
| 9 | Poly vinyl pyrrolidone | 0.25 | 0.25 | 0.25 |
| 10 | Ethoxylated nonyl phenol 9.5 moles | 0.00 | 3.00 | 0.00 |
| 11 | Ethoxylated sorbitan monooleate 20 moles | 0.00 | 0.00 | 2.25 |
|  | Comments: | Suspensibility & Dispersibility of granules are very low. | Suspensibility & Dispersibility of granules are very low. | Suspensibility & Dispersibility of granules are very low. |

Further experiments were conducted with Polyoxyethylene alkyl ether also called EO/PO surfactant normally unused in DF formulations. Surprising results were obtained with the said surfactant with improved dispersibility and suspensibility.

TABLE 9

Effect of various concentrations of EO/PO on granule quality.

| Sr. No. | % Active | Quantity of EO/PO | Ratio of Active %:EO/PO % | Comments |
|---|---|---|---|---|
| 1 | 0.1064 | 1.50 | 1:14.09 | (A) |
| 2 | 1.064 | 1.70 | 1:1.598 | (A) |
| 3 | 5.32 | 1.75 | 1:0.329 | (A) |
| 4 | 10.64 | 2.00 | 1:0.188 | (A) |
| 5 | 15.96 | 2.50 | 1:0.157 | (A) |
| 6 | 26.60 | 2.75 | 1:0.103 | (A) |
| 7 | 37.24 | 3.50 | 1:0.094 | (A) |
| 8 | 42.56 | 3.75 | 1:0.088 | (A) |
| 9 | 47.88 | 4.00 | 1:0.084 | (B) |
| 10 | 53.20 | 4.50 | 1:0.085 | (B) |

(A) Good dispersibility & suspensibility; dispersibility = 96-98%; suspensibility = 88-90%.
(B) Soft & slightly sticky granules with decreasing dispersibility & suspensibility; dispersibility = 80-85%; suspensibility = 74-78%.

The working range of EO/PO surfactants was found to be optimal between 1.5 to 3.75%. Within this range good emulsification of the liquid active ingredient was observed.

To further improve the dispersibility and suspensibility of silica and kaolin, styrene acrylic co-polymer was considered.

TABLE 10

Effect of various concentrations of Styrene acrylic copolymer on granule quality.

| Sr. No. | % Active | Ratio of Silica:Kaolin | Quantity of styrene acrylic copolymer | Comments |
|---|---|---|---|---|
| 1 | 0.1064 | 1:40.655 | 5 | (A) |
| 2 | 1.064 | 1:26.45 | 6 | (A) |
| 3 | 5.32 | 1:18.525 | 7 | (A) |
| 4 | 10.64 | 1:13.556 | 7 | (A) |
| 5 | 15.96 | 1:8.637 | 8 | (A) |
| 6 | 26.60 | 1:4.682 | 8 | (A) |
| 7 | 37.24 | 1:3.015 | 9 | (A) |
| 8 | 42.56 | 1:2.572 | 10 | (A) |
| 9 | 47.88 | 1:0.977 | 11 | (B) |
| 10 | 53.20 | 1:0.711 | 13 | (B) |

(A) Good dispersibility & suspensibility; dispersibility = 96-98%; suspensibility = 88-90%.
(B) Soft & slightly sticky granules with decreasing dispersibility & suspensibility; dispersibility = 80-85%; suspensibility = 74-78%.

5 to 10% of Styrene acrylic copolymer was found to give good dispersibility and suspensibility for the optimal ratio of silica and kaolin. A combination of EO/PO with styrene copolymer was studied for further improvement of the granule dispersibility and suspensibility.

TABLE 11

Effect of a combination of various concentrations of EO/PO and Styrene acrylic copolymer.

| Sr. No. | % Active | Ratio of Silica:Kaolin | Quantity of EO/PO/Styrene acrylic copolymer | Observations |
|---|---|---|---|---|
| 1 | 0.1064 | 1:40.655 | 1.50/5 | (A) |
| 2 | 1.064 | 1:26.45 | 1.70/6 | (A) |
| 3 | 5.32 | 1:18.525 | 1.75/7 | (A) |
| 4 | 10.64 | 1:13.556 | 2.00/7 | (A) |
| 5 | 15.96 | 1:8.637 | 2.50/8 | (A) |
| 6 | 26.60 | 1:4.682 | 2.75/8 | (A) |
| 7 | 37.24 | 1:3.015 | 3.50/9 | (A) |
| 8 | 42.56 | 1:2.572 | 3.75/10 | (A) |
| 9 | 47.88 | 1:0.977 | 4.00/11 | (B) |
| 10 | 53.20 | 1.0.711 | 4.50/13 | (B) |

(A) Good dispersibility & suspensibility; dispersibility = 98-99%; suspensibility = 90-91%.
(B) Soft & slightly sticky granules with decreasing dispersibility & suspensibility; dispersibility = 82-85%; suspensibility = 75-77%.

Surprisingly it was observed that granules with emulsifiable concentrate (EC) provided the requisite dispersibility, however the granules were unable to be formed. This surprising observation of use of emulsifier with the above combination of kaolin and silica provided the most unobvious results of free-flowing dispersible granules at high concentrations of liquid actives.

Polyoxyethlene alkyl ether, the block copolymer of ethylene oxide and propylene oxide is a surfactant having a comparable hydrophilic chains length than those of most other surfactants and they are flexible. They bind water avidly by hydrogen bond acceptor interactions with ether-linked oxygen. These long, strongly hydrated flexible chains are relatively incompressible and form a barrier to hydrophobic surfaces approaching one another. As emulsifying and/or dispersing agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylarylsulphonates, alkylsulphates, arylsulphonates, their hydrolysis products & salts. More precisely, the use of polyoxyethlene alkyl ether in this case helped to provide a solid composition with at least 60% dispersibility and suspensibility despite high concentrations of viscous liquid pesticide. A mixture prepared by adding active ingredient with at least one polyoxyethylene alkyl ether surfactant helps to cover the treated surface area uniformly.

By the term "wetting agent" is meant a compound which permits the granule to rapidly wet into the water, and, more precisely, a compound which, when mixed in selected proportions with agriculturally active compounds, in the form of granules, give a mixture which has a wettability time of less than 2 minutes. This wetting agent can be an ionic or non-ionic agent or a mixture of such surface-active agents.

Compounds which are usable as wetting agents and which can be cited are, for example, the alkylarylsulphonate-type salts, in particular the alkali metal alkylnaphthalene sulphonates, the salts of polycarboxylic acids, polycondensates of ethylene oxide with fatty alcohols or with fatty acids or with fatty amines, or substituted phenols (in particular alkylphenols or arylphenols), and salts of esters of sulphosuccinic acids.

By the term "dispersing agent" is meant a compound which ensures that the particles remain suspended in the application mixture and which allows rapid disintegration of the granule in the water. More precisely, by dispersing agent is meant a compound which, when intimately mixed in selected proportions with agriculturally active compounds, in the form of granules, gives a mixture which has a suspensibility of more than 50%. The dispersing agent can be an ionic or non-ionic agent or a mixture of such surface-active agents.

As compounds which are suitable as dispersing agents there may be cited, for example, arylsulphonate-type polymers, in particular the alkali metal polynaphthalenesulphonates obtained by condensation of (alkyl)arylsulphonates with formaldehyde, the lignosulphonates, the polyphenylsulphonates, salts of polyacrylic acids, salts of lignosulphonic acids, salts of phenolsulphonic acids or naphthalenesulphonic acids, taurine derivatives (in particular alkyltaurates), phosphoric esters of alcohols or of polycondensates of ethylene oxide and phenols, esters of fatty acids and polyols, and the derivatives of the preceding compounds which have sulphate, sulphonate and phosphate functions.

The term "binders" refers to all binders which are suitable for solid compositions such as in water-dispersible solid formulations. The following are preferably suitable in this context: methylcellulose, sugars, dextrin, starch, alginates, glycols, polyvinyl pyrrolidone, ligninsulphonate, gum arabic, polyvinyl alcohol and polyvinyl acetate, water, or a solution containing dissolved wetting and dispersing agents.

In the step additional inert fillers may be used. Such "inert fillers" refer to a solid organic or inorganic material, natural or synthetic, with which the active substance is combined so as to facilitate the specific application of the granulated product. This filler is therefore generally inert and acceptable. The filler can be selected for example from amongst clay, diatomaceous earth, kaolin clay, the natural or synthetic silicates, silica, precipitated silica, soluble or insoluble mineral salts, organic derivatives, and polysaccharide compounds such as starch, cellulose, aliginates, soluble mineral salts, sugars and lactose or a combination thereof. The inert fillers which can be used are hydrophilic fillers which have a disintegrating action, that is to say which facilitate the adsorption as well as absorption of active ingredient and also facilitate the dispersion and suspension of the granule according to the invention in the presence of water.

Besides the product used for granulation the product (first compound) may contain at least a second active compound of a type which differs from the first compound, which has the aim of widening the spectrum of the first one. In the case of agro chemicals used the first and second compound may be a contact pesticide, which act by contact with the plants/pests. This second agent may be present in the solid composition prepared by the process of the proposed invention in an amount between 0.1 to 40.0%. The first agricultural compound may be present in quantities, preferably between 0.1 to 50.0%, the other ingredients in the end product being the wetting agent, dispersing agent and inert fillers. Besides the above-described ingredients the granulated product may also contain 10.0 to 99.80% of suitable additives, such as anti-foams, sequestering agents, stabilizers, penetrating agents, adhesives, anti-caking agents, colorants, and others.

The process of the proposed invention is generally carried out starting with the mixing of an active ingredient, with at least polyoxyethlene alkyl ether surfactants to obtain a liquid mixture. There after the preparation of the powders of wetting agent, dispersing agent, binder and inert fillers by mixing is done. This mixing of the powders may be done in suitable mixers.

According to the proposed invention adding of the liquid mixture is done over the powder prepared. After complete addition of the liquid mixture these ingredients are mixed thoroughly to obtain a homogenous powdery mixture. This powdery mixture can also be considered as one of the forms of invented solid composition which is in the form of powder. If the granulated product is required then this is achieved by continuing the mixing for an additional time, after spraying was over. Thereafter granulation of the mixture is performed by using water as a granulating liquid. Then the fine particles are separated from oversized particles. If required, the fine and oversized particles are recycled and drying of the granules is done, as required, in a drier like equipment like Fluidized bed dryer to a moisture content below 2% w/w. Again sieving of the dried granules is done by using vibratory sieve to finally remove any fine and or oversize granules. The fine and the oversize separated particles can be recycled to the granulator after drying and grinding to suitable particle size.

According to the proposed invention, the powder taken in the container of the apparatus is mixed with granulating liquid, from 1 to 30%, preferably 5 to 15% of the required quantities. This moistened powder has the consistency of a non drifting dust. This is further processed in the container with the addition of remaining quantity of the granulating liquid in such a way as to obtain the granulated product.

The granules prepared by the process according to the proposed invention are therefore concentrated products. The granulated agricultural products which are prepared according to the process of the proposed invention which are diluted by the agriculturalists in containers which contain water for application. These diluted mixtures are usually applied at 5 to 1000 l/ha.

The use of solvents such as petroleum solvents, methylene dichloride and the like resulted in phase separation on dilution with water. Surprisingly it was possible to formulate the high dispersible and suspensible granules even without the use of solvents by careful combination of selected liquid surfactants along with a specific composition of inert ingredients on which the liquid active is adsorbed.

The compositions of the present invention actually fall into the category of dispersible granules comprising an intrinsic combination of granule, surfactant/s, oil (the active ingredient which is in the form of a viscous liquid is considered as the oil which is emulsified) and the active ingredient which is adsorbed on the solid inert ingredient/s. Thus it was possible to produce free-flowing dispersible granules even without the use of solvents and thus eliminate the possibility of flammability during handling, processing, storage and transportation and irritation to skin of human body and make an environment friendly composition.

In the present invention, active ingredients used may be in the range of 0.1-50% by weight of composition. The solid composition has a long activity and quick-acting property with residual effectiveness and improvement in stickiness, fluidity and bulkiness, also from the view point of physical properties of the formulation.

The details of the invention are given in the Examples given below which are given only to illustrate the invention and hence they should not be construed to limit the scope of the invention

Example 1

The composition was designed to test the effect of solid surfactants such as Sodium naphthalene formaldehyde condensate and Sodium naphthalene sulfonate on the performance of the granules.

| Ingredients | Function | % w/w |
|---|---|---|
| Permethrin Technical | Active Ingredient | 26.66 |
| Sodium naphthalene formaldehyde condensate | Surfactant | 4.00 |
| Sodium naphthalene sulfonate | Wetting agent | 2.00 |
| Tri sodium phosphate | Stabilizer | 1.00 |
| Sodium stearate | Lubricant | 1.00 |
| Poly vinyl alcohol | Binder | 0.50 |
| Precipitated Silica | Inert filler | 18.84 |
| Kaolin | Inert filler | 46.01 |
| Total | | 100.00 |

It was observed that the mixture became wet and granules obtained were soft. The granules gave 1 ml sediment in 5 minutes after dilution with water, therefore giving low dispersibility and suspensibility. It was further observed that even after milling of premix to reduce the particle size, the low dispersibility and suspensibility did not improve. The formulation was found to be unacceptable.

Example 2

The composition of Example 1 which resulted in granules of sticky nature was modified to increase the quantity of silica to 46.01% to improve the flowability of the granules.

| Ingredients | Function | % w/w |
|---|---|---|
| Permethrin Technical | Active Ingredient | 26.66 |
| Sodium naphthalene formaldehyde condensate | Surfactant | 4.00 |
| Sodium naphthalene sulfonate | Wetting agent | 2.00 |
| Tri sodium phosphate | Stabilizer | 1.00 |
| Sodium stearate | Lubricant | 1.00 |
| Poly vinyl alcohol | Binder | 0.50 |
| Precipitated Silica | Inert filler | 46.01 |
| Kaolin | Inert filler | 18.84 |
| Total | | 100.00 |

The above composition was not workable because of decreased dispersibility of granules. The high silica content was able to decrease the wettness of the granules, but was unable to provide a suitable degree of dispersibility. In fact the dispersibility was found to be even lower than earlier example.

Example 3

The composition was modified to include organic solvents in the formulation.

| Ingredients | % w/w |
|---|---|
| Permethrin Technical | 26.66 |
| POE of alkyl ether containing alkyl phenol ethoxylate | 2.75 |
| Calcium dodecyl benzene sulfonate | 0.83 |
| Petroleum solvent | 10.00 |
| Styrene acrylic copolymer | 8.00 |
| Dimethyl polysiloxane, 30% emulsion | 0.50 |
| Polyvinyl pyrrolidone | 0.25 |
| Precipitated Silica | 10.00 |
| Kaolin | 36.01 |
| Total | 100.00 |

The above composition was unable to provide the required degree of dispersibility and suspensibility to the granules.

Example 4

Experimental trials were further conducted for determining the optimal quantity of POE of alkyl ether containing alkyl phenol ethoxylate in the formulation. All parameters remaining the same, Composition A contained 1.75% of POE of alkyl ether containing alkyl phenol ethoxylate, Composition B contained 2.75% of POE of alkyl ether containing alkyl phenol ethoxylate and Composition C contained 3.75% of POE of alkyl ether containing alkyl phenol ethoxylate.

| Ingredients | A | B | C |
|---|---|---|---|
| Permethrin Technical | 26.66 | 26.66 | 26.66 |
| POE of alkyl ether containing alkyl phenol ethoxylate | 1.75 | 2.75 | 3.75 |
| Calcium dodecyl benzene sulfonate | 0.83 | 0.83 | 0.83 |
| Precipitated Silica | 10.00 | 10.00 | 10.00 |
| Sodium naphthalene sulfonate | 5.00 | 5.00 | 5.00 |
| Styrene acrylic copolymer | 8.00 | 8.00 | 8.00 |
| Dimethyl polysiloxane, 30% emulsion | 0.50 | 0.50 | 0.50 |
| Homopolymer of Vinylpyrrolidone | 0.25 | 0.25 | 0.25 |
| Kaolin | 52.01 | 46.01 | 40.01 |
| Total | | 100.00 | |

From the above trials, it was observed that composition A and C showed reduced emulsification of permethrin. Composition B showed optimal results and was considered as most appropriate for the composition.

Composition B was tested for required parameters the following results were observed:

| | |
|---|---|
| Suspensibility (% w/w): | 87.50 |
| Dispersibility (% w/w): | 72 |
| Wettability (sec.): | 7 |
| Dustiness (% w/w): | 0.20 |

Example 5

In order to arrive at an optimal concentration of silica in the composition, three compositions were designed and designated as A, B and C with variations in amounts of silica.

| Ingredients | A | B | C |
|---|---|---|---|
| Permethrin Technical | 26.66 | 26.66 | 26.66 |
| POE of alkyl ether containing alkyl phenol ethoxylate | 2.75 | 2.75 | 2.75 |
| Calcium dodecyl benzene sulfonate | 0.83 | 0.83 | 0.83 |
| Precipitated Silica | 5.00 | 10.00 | 15.00 |
| Sodium naphthalene sulfonate | 5.00 | 5.00 | 5.00 |
| Styrene acrylic copolymer | 8.00 | 8.00 | 8.00 |
| Dimethyl polysiloxane, 30% emulsion | 0.50 | 0.50 | 0.50 |
| Homopolymer of Vinylpyrrolidone | 0.25 | 0.25 | 0.25 |
| Kaolin | 51.01 | 46.01 | 41.01 |
| Total | | 100.00 | |

Composition A with 5% silica resulted in slightly sticky granules having average suspensibility. Composition C resulted in granules with good flowability but reduced suspensibility. Composition B with 10% silica resulted in granules with very good flowability and suspensibility. The optimum concentration of 10% was selected.

Example 6

Experimental trials were conducted using lactose as a soluble carrier instead of kaolin to improve suspensibility and dispersibility,

| Ingredients | Function | % w/w |
|---|---|---|
| Permethrin Technical | Active Ingredient | 26.66 |
| POE of alkyl ether containing alkyl phenol ethoxylate | Surfactant | 2.75 |
| Calcium dodecyl benzene sulfonate | Surfactant | 0.83 |
| Precipitated Silica | Inert filler | 10.00 |
| Sodium naphthalene sulfonate | Wetting agent | 5.00 |
| Styrene acrylic copolymer | Dispersant | 8.00 |
| Dimethyl polysiloxane, 30% emulsion | Defoamer | 0.50 |
| Homopolymer of Vinylpyrrolidone | Binder | 0.25 |
| Lactose | Inert filler | 46.01 |
| Total | | 100.00 |

The resultant granules were sticky in nature with reduced flowability and could not be further processed.

Example 7

Trials were conducted using varying amounts of styrene acrylic co-polymer which is crucial for suspending the inert carrier silica and kaolin. Composition A contains 5% Styrene acrylic copolymer; composition B contains 8% Styrene acrylic copolymer and composition C contains 13% Styrene acrylic copolymer.

| Ingredients | A | B | C |
|---|---|---|---|
| Permethrin Technical | 26.66 | 26.66 | 26.66 |
| POE of alkyl ether containing alkyl phenol ethoxylate | 2.75 | 2.75 | 2.75 |
| Calcium dodecyl benzene sulfonate | 0.83 | 0.83 | 0.83 |
| Precipitated Silica | 10.00 | 10.00 | 10.00 |
| Sodium naphthalene sulfonate | 5.00 | 5.00 | 5.00 |
| Styrene acrylic copolymer | 5.00 | 8.00 | 13.00 |
| Dimethyl polysiloxane, 30% emulsion | 0.50 | 0.50 | 0.50 |
| Homopolymer of Vinylpyrrolidone | 0.25 | 0.25 | 0.25 |
| Kaolin | 55.01 | 46.01 | 35.01 |
| Total | | 100.00 | |

It was observed that for composition A there was a drop in suspensibility. Composition B had ideal suspensibility. In composition C excess foaming was observed. It was concluded that 8% Styrene acrylic copolymer was optimal for attaining desirable suspensibility of the formulation.

Example 8

Step I

Permethrin Technical (26.66% w/w), POE of alkyl ether containing alkyl phenol ethoxylate (2.75% w/w), Calcium dodecyl benzene sulfonate (0.83% w/w) and Dimethyl polysiloxane, 30% emulsion (0.5% w/w) were weighed and transferred in a vessel having homogenizer to handle moderate viscous liquid. The mixture was homogenized for 30 min. at 30-400° C.

Step II

Styrene acrylic copolymer (8.00% w/w), Sodium naphthalene sulfonate (5.00% w/w), pre ground Kaolin (46.01% w/w), Homopolymer of Vinylpyrrolidone (0.25% w/w), Precipitated Silica (10.00% w/w) are transferred in appropriate blender having spray arrangement. The mixture was blended for 10 min. along with the spraying of the liquid mixture of step I over it. The blending was continued for further 10 min. after spraying was completed.

Step III

Using appropriate granulator and mechanized water spray system, the product of step II was granulated to get non-dusty, free flowing, storage stable granules.

The ingredients used are given below in table 1.

The end product of each lot of granulated wet granules was first conditioned. The fines separated were re-cycled to granulator. Oversized granules were dried and ground to suitable particle size to re-cycle on granulator.

The desired sized wet/conditioned granules were dried using equipment like fluidized bed drier to moisture content below 2% w/w.

The dried granules were sieved by using vibratory sieve, the fines and oversized separated were recycled in granulator after drying and grinding to suitable particle size. The representative composite sample of dried and required dust free granules was analyzed.

TABLE 1

| Ingredients | Function | % w/w |
|---|---|---|
| Permethrin Technical | Active Ingredient | 26.66 |
| POE of alkyl ether containing alkyl phenol ethoxylate | Surfactant | 2.75 |
| Calcium dodecyl benzene sulfonate | Surfactant | 0.83 |
| Precipitated Silica | Inert filler | 10.00 |
| Sodium naphthalene sulfonate | Wetting agent | 5.00 |
| Styrene acrylic copolymer | Dispersant | 8.00 |
| Dimethyl polysiloxane, 30% emulsion | Defoamer | 0.50 |
| Homopolymer of Vinylpyrrolidone | Binder | 0.25 |
| Kaolin | Inert filler | 46.01 |
| Total | | 100.00 |

The same procedure as given in example 1 was repeated with different % w/w of Permethrin technical, Precipitated Silica, and Kaolin to get granules with improved storage stability, suspensibility, dispersibility as well as wettability of the granules.

The % w/w for the ingredients involved in different processes is given below: (Examples 2-Examples 9)

Example 9

| Ingredients | Function | % w/w |
|---|---|---|
| Permethrin Technical | Active Ingredient | 0.11 |
| POE of alkyl ether containing alkyl phenol ethoxylate | Surfactant | 2.75 |
| Calcium dodecyl benzene sulfonate | Surfactant | 0.83 |
| Precipitated Silica | Inert filler | 2.0 |
| Sodium naphthalene sulfonate | Wetting agent | 5.00 |
| Styrene acrylic copolymer | Dispersant | 8.00 |
| Dimethyl polysiloxane, 30% emulsion | Defoamer | 0.5 |
| Homopolymer of Vinylpyrrolidone | Binder | 0.25 |
| Kaolin | Inert filler | 80.56 |
| Total | | 100.00 |

Example 10

| Ingredients | Function | % w/w |
|---|---|---|
| Permethrin Technical | Active Ingredient | 0.53 |
| POE of alkyl ether containing alkyl phenol ethoxylate | Surfactant | 2.75 |
| Calcium dodecyl benzene sulfonate | Surfactant | 0.83 |
| Precipitated Silica | Inert filler | 2.5 |
| Sodium naphthalene sulfonate | Wetting agent | 5.00 |
| Styrene acrylic copolymer | Dispersant | 8.00 |
| Dimethyl polysiloxane, 30% emulsion | Defoamer | 0.5 |
| Homopolymer of Vinylpyrrolidone | Binder | 0.25 |
| Kaolin | Inert filler | 79.64 |
| Total | | 100.00 |

Example 11

| Ingredients | Function | % w/w |
|---|---|---|
| Permethrin Technical | Active Ingredient | 5.32 |
| POE of alkyl ether containing alkyl phenol ethoxylate | Surfactant | 2.75 |
| Calcium dodecyl benzene sulfonate | Surfactant | 0.83 |
| Precipitated Silica | Inert filler | 4.00 |
| Sodium naphthalene sulfonate | Wetting agent | 5.00 |
| Styrene acrylic copolymer | Dispersant | 8.00 |
| Dimethyl polysiloxane, 30% emulsion | Defoamer | 0.50 |
| Homopolymer of Vinylpyrrolidone | Binder | 0.25 |
| Kaolin | Inert filler | 73.35 |
| Total | | 100.00 |

Example 12

| Ingredients | Function | % w/w |
|---|---|---|
| Permethrin Technical | Active Ingredient | 31.92 |
| POE of alkyl ether containing alkyl phenol ethoxylate | Surfactant | 2.75 |
| Calcium dodecyl benzene sulfonate | Surfactant | 0.83 |
| Precipitated Silica | Inert filler | 10 |
| Sodium naphthalene sulfonate | Wetting agent | 5.00 |
| Styrene acrylic copolymer | Dispersant | 8.00 |
| Dimethyl polysiloxane, 30% emulsion | Defoamer | 0.5 |
| Homopolymer of Vinylpyrrolidone | Binder | 0.25 |
| Kaolin | Inert filler | 40.75 |
| Total | | 100.00 |

Example 13

| Ingredients | Function | % w/w |
|---|---|---|
| Permethrin Technical | Active Ingredient | 37.24 |
| POE of alkyl ether containing alkyl phenol ethoxylate | Surfactant | 2.75 |
| Calcium dodecyl benzene sulfonate | Surfactant | 0.83 |
| Precipitated Silica | Inert filler | 12 |
| Sodium naphthalene sulfonate | Wetting agent | 4.00 |
| Styrene acrylic copolymer | Dispersant | 7.00 |
| Dimethyl polysiloxane, 30% emulsion | Defoamer | 0.5 |
| Homopolymer of Vinylpyrrolidone | Binder | 0.25 |
| Kaolin | Inert filler | 35.43 |
| Total | | 100.00 |

Example 14

| Ingredients | Function | % w/w |
|---|---|---|
| Permethrin Technical | Active Ingredient | 42.56 |
| POE of alkyl ether containing alkyl phenol ethoxylate | Surfactant | 2.75 |
| Calcium dodecyl benzene sulfonate | Surfactant | 0.83 |
| Precipitated Silica | Inert filler | 12 |
| Sodium naphthalene sulfonate | Wetting agent | 4.00 |
| Styrene acrylic copolymer | Dispersant | 7.00 |
| Dimethyl polysiloxane, 30% emulsion | Defoamer | 0.5 |
| Homopolymer of Vinylpyrrolidone | Binder | 0.25 |
| Kaolin | Inert filler | 30.11 |
| Total | | 100.00 |

Example 15

| Ingredients | Function | % w/w |
|---|---|---|
| Permethrin Technical | Active Ingredient | 47.88 |
| POE of alkyl ether containing alkyl phenol ethoxylate | Surfactant | 2.75 |
| Calcium dodecyl benzene sulfonate | Surfactant | 0.83 |
| Precipitated Silica | Inert filler | 20.0 |
| Sodium naphthalene sulfonate | Wetting agent | 3.0 |
| Styrene acrylic copolymer | Dispersant | 6.0 |
| Dimethyl polysiloxane, 30% emulsion | Defoamer | 0.5 |
| Homopolymer of Vinylpyrrolidone | Binder | 0.25 |
| Kaolin | Inert filler | 18.79 |
| Total | | 100.00 |

Example 16

| Ingredients | Function | % w/w |
|---|---|---|
| Permethrin Technical | Active Ingredient | 53.20 |
| POE of alkyl ether containing alkyl phenol ethoxylate | Surfactant | 2.75 |
| Calcium dodecyl benzene sulfonate | Surfactant | 0.83 |
| Precipitated Silica | Inert filler | 20.0 |
| Sodium naphthalene sulfonate | Wetting agent | 3.0 |
| Styrene acrylic copolymer | Dispersant | 6.00 |
| Dimethyl polysiloxane, 30% emulsion | Defoamer | 0.5 |
| Homopolymer of Vinylpyrrolidone | Binder | 0.25 |
| Kaolin | Inert filler | 13.47 |
| Total | | 100.00 |

The characteristic outcome of the employment of the process of the proposed invention is the dispersing and wetting of almost 100% of the particles with a minimum of water.

The Table 2 and 3 below show the advantages of the present invention in terms of wettability, dispersibility & suspensibility:

i) Wettability time of less than 2 minutes, preferably less than 1 minute;
ii) Dispersibility of more than 60%, preferably more than 70%;
iii) Suspensibility of more than 60%, preferably more than 75%;
iv) Dustiness less than 1% w/w, preferably less than 0.6% w/w.

TABLE 2

| Sr. No. | Ingredients | Comp. No. 8 | Comp. No. 9 | Comp. No. 10 | Comp. No. 11 |
|---|---|---|---|---|---|
| 1 | Appearance | Cream colored free flowing granules | Cream colored free flowing granule | Cream colored free flowing granule | Cream colored free flowing granule |
| 2 | Active content (% w/w) | 0.105 | 0.51 | 5.02 | 25.2 |
| 3 | Suspensibility (% w/w) | 94.20 | 93.89 | 92.50 | 87.50 |
| 4 | Dispersibility (% w/w) | 78 | 75 | 73 | 72 |
| 5 | pH (1% aq.solution) | 7.65 | 7.55 | 7.45 | 7.40 |
| 6 | Wet sieve (% retained on 75µ test sieve) | 0.12 | 0.11 | 0.13 | 0.11 |
| 7 | Wettability (sec.) | 15 | 10 | 8 | 7 |
| 8 | Dustiness (% w/w) | 0.5 | 0.3 | 0.25 | 0.20 |

TABLE 3

| Sr. No. | Ingredients | Comp. No. 11 | Comp. No. 12 | Comp. No. 13 | Comp. No. 14 | Comp. No. 15 |
|---|---|---|---|---|---|---|
| 1 | Appearance | Cream colored free flowing granule | Cream colored free flowing granule | Cream colored free flowing granule | Cream colored slightly sticky granules | Cream colored slightly sticky granules |
| 2 | Active content (% w/w) | 30.12 | 35.02 | 40.15 | 45.17 | 50.14 |
| 3 | Suspensibility (% w/w) | 78.25 | 72.00 | 65.00 | 60.00 | 57.00 |
| 4 | Dispersibility (% w/w) | 72 | 70 | 65 | 62 | 60 |
| 5 | pH (1% aq.solution) | 7.35 | 7.33 | 7.25 | 7.20 | 7.22 |
| 6 | Wet sieve (% retained on 75µ test sieve) | 0.10 | 0.10 | 0.12 | 0.14 | 0.15 |
| 7 | Wettability (sec.) | 7 | 6 | 5 | 5 | 4 |
| 8 | Dustiness (% w/w) | 0.18 | 0.20 | 0.19 | 0.20 | 0.18 |

The table 4 below shows the advantages of the present invention in terms of storage stability:

TABLE 4

| Sr. No. | Parameters Stage | Batch No. 1 Cream colored granules | | | Batch No. 2 Cream colored granules | | | Batch No. 3 Cream colored granules | | |
|---|---|---|---|---|---|---|---|---|---|---|
| | | 0 day | 7 days AHS | 14 days AHS | 0 day | 7 days AHS | 14 days AHS | 0 day | 7 days AHS | 14 days AHS |
| 1 | Active content (% w/w) | 25.87 | 25.83 | 25.84 | 25.87 | 25.83 | 25.84 | 25.54 | 25.81 | 25.41 |
| 2 | Suspensibility (% w/w) | 80.39 | 79.27 | 78.62 | 79.09 | 76.27 | 76.23 | 76.31 | 75.41 | 77.93 |
| 3 | Dispersibility (% w/w) | 73 | 70 | 69 | 72 | 69 | 68 | 71 | 69 | 68 |
| 4 | pH 1% aq.solution | 7.40 | 7.45 | 7.43 | 7.32 | 7.25 | 7.24 | 7.28 | 7.27 | 7.30 |
| 5 | Wet sieve (% retained on 75 u test sieve) | 0.1 | 0.15 | 0.17 | 0.12 | 0.16 | 0.20 | 0.1 | 0.12 | 0.15 |
| 6 | Wettability in sec. | 5 | 6 | 5 | 6 | 5 | 5 | 6 | 6 | 7 |
| 7 | Dustiness (% w/w) | 0.20 | 0.21 | 0.18 | 0.18 | 0.20 | 0.19 | 0.21 | 0.20 | 0.22 |

In addition to above, following are the further advantageous features for the present invention:

i) The process affords complete control on the size of the granules produced.
ii) The drying temperature is also less, in-between 50 to 60° C., leading to energy savings as compared to conventional processes.
iii) The process does not require the grinding of the active ingredient along with the inert ingredients.
iv) The process affords multi material processing leading to better solid and granulated product of combined active ingredients.
v) The process helps to convert the liquid viscous pesticide into solid composition and product.

The present granular pesticidal formulation is used for controlling pests. When the pesticidally active compound is an insecticidal compound, they are preferably used for vegetables or fruit trees. The present granular pesticidal formulation is used as water dispersible granules, to be precise; the present granular pesticidal formulation is diluted with water and then applied to crop, soil or the like with a sprayer or the like.

Although this invention has been described with respect to specific embodiments, the details thereof are not to be construed as limitations, for it will be apparent that various equivalents, changes and modifications may be resorted to without departing from the spirit and scope of this invention. It is understood that such equivalent embodiments are intended to be included within the scope of this invention.

We claim:

1. A free flowing water-dispersible dry granule formulation comprising:
   (a) liquid permethrin in an amount of up to 50% weight/weight adsorbed on a specific composition of inert fillers of silica and inert clay kaolin, wherein the amount of silica is 10% weight/weight;
   (b) 2.75% weight/weight POE of alkyl ether containing alkyl phenol ethoxylate and 8% weight/weight styrene acrylic copolymer and optionally containing (c) inert formulation adjuvants.

2. The free-flowing dry granular formulation according to claim 1, wherein the said inert formulation adjuvants are selected from at least one of additional surfactants, dispersing agents, defoamers, wetting agents and binders.

3. The free-flowing dry granular formulation according to claim 2 wherein said additional surfactant is calcium dodecyl benzene sulfonate.

4. The free-flowing dry granular formulation according to claim 2 wherein the defoamer is dimethyl polysiloxane.

5. The free-flowing dry granular formulation according to claim 2 wherein the wetting agent is sodium naphthalene sulfonate.

6. The free-flowing dry granular formulation according to claim 2 wherein the binder is selected from vinyl acetate homopolymer, homopolymers of vinyl pyrrolidone and alkylated vinyl pyrrolidine copolymers.

7. A formulation of free-flowing granules comprising 26.66% weight/weight permethrin, precipitated silica in an amount of 10.0% weight/weight, 2.75% weight/weight of POE of alkyl ether containing alkyl phenol ethoxylate, 8% weight/weight styrene acrylic copolymer, calcium dodecyl benzene sulfonate, dimethyl polysiloxane, sodium naphthalene sulfonate and homopolymer of vinylpyrrolidone.

* * * * *